United States Patent
Mahoney et al.

(10) Patent No.: US 8,025,682 B2
(45) Date of Patent: Sep. 27, 2011

(54) METHOD AND SYSTEM FOR SECURING A ROD TO A BONE ANCHOR WITH A CONNECTOR

(75) Inventors: Michael Mahoney, Middletown, RI (US); Christopher L. Ramsay, West Wareham, MA (US); David Greg Anderson, Moorestown, NJ (US); Steven Ludwig, Baltimore, MD (US); Michael Wang, Miami, FL (US)

(73) Assignee: DePuy Spine, Inc., Raynham, MA (US)

( * ) Notice: Subject to any disclaimer, the term of this patent is extended or adjusted under 35 U.S.C. 154(b) by 1059 days.

(21) Appl. No.: 11/897,566

(22) Filed: Aug. 31, 2007

(65) Prior Publication Data

US 2009/0062859 A1 Mar. 5, 2009

(51) Int. Cl.
*A61B 17/70* (2006.01)
(52) U.S. Cl. ........ 606/264; 606/278; 606/301; 606/305; 606/308
(58) Field of Classification Search ................ 606/264, 606/265, 267, 270, 272, 276, 277
See application file for complete search history.

(56) References Cited

U.S. PATENT DOCUMENTS

| | | | |
|---|---|---|---|
| 4,653,481 A | 3/1987 | Howland et al. | |
| 5,306,275 A | 4/1994 | Bryan | |
| 5,474,551 A | 12/1995 | Finn et al. | |
| 5,584,834 A | 12/1996 | Errico et al. | |
| 5,609,592 A | 3/1997 | Brumfield et al. | |
| 5,624,441 A | 4/1997 | Sherman et al. | |
| 5,984,922 A | 11/1999 | McKay | |
| 6,468,276 B1 | 10/2002 | McKay | |
| 6,562,038 B1 | 5/2003 | Morrison | |
| 6,626,906 B1 | 9/2003 | Young | |
| 6,726,692 B2 | 4/2004 | Bette et al. | |
| 6,770,075 B2 | 8/2004 | Howland | |
| 6,964,665 B2 | 11/2005 | Thomas et al. | |

(Continued)

FOREIGN PATENT DOCUMENTS

EP 1339337 B1 9/2003

(Continued)

OTHER PUBLICATIONS

Ebara, Sohei et al., "A New System for the Anterior Restoration and Fixation of Thoracic Spinal Deformities Using an Endoscopic Approach," *Spine*, vol. 25(7):876-883 (2000).

*Primary Examiner* — Eduardo C Robert
*Assistant Examiner* — Ellen C Hammond
(74) *Attorney, Agent, or Firm* — Nelson Mullins Riley & Scarborough LLP

(57) ABSTRACT

A rod anchoring system including a bone anchor and a connector is provided. The connector of the rod anchoring system is configured to be inserted in one orientation and then transitioned to a second orientation to connect the rod to the anchor. The bone anchor includes a detachable extension shaft that acts as a guide for inserting the connector. In use, once the bone anchor has been implanted at a target site on a vertebra, the connector is placed onto the extension shaft and slid along its length in a first orientation to insert the connector. Once the connector is at the implant site, it is transitioned from the first orientation to the second orientation to connect the rod to the anchor.

13 Claims, 14 Drawing Sheets

U.S. PATENT DOCUMENTS

| | | |
|---|---|---|
| RE39,035 E | 3/2006 | Finn et al. |
| 7,166,108 B2 | 1/2007 | Mazda et al. |
| 7,766,943 B1 * | 8/2010 | Fallin et al. .................. 606/264 |
| 7,780,706 B2 * | 8/2010 | Marino et al. ................ 606/264 |
| 2002/0169450 A1 * | 11/2002 | Lange ............................ 606/61 |
| 2004/0236330 A1 | 11/2004 | Purcell et al. |
| 2006/0089651 A1 | 4/2006 | Trudeau et al. |
| 2006/0111730 A1 | 5/2006 | Hay |
| 2006/0155278 A1 | 7/2006 | Warnick |
| 2006/0173456 A1 | 8/2006 | Hawkes et al. |
| 2006/0235389 A1 * | 10/2006 | Albert et al. ................... 606/61 |
| 2006/0264934 A1 | 11/2006 | Fallin |
| 2006/0282074 A1 | 12/2006 | Renaud et al. |

FOREIGN PATENT DOCUMENTS

| | | |
|---|---|---|
| EP | 1405606 A2 | 4/2004 |
| WO | WO-98/49961 A1 | 11/1998 |
| WO | WO-2004/080318 A1 | 9/2004 |
| WO | WO-2006/023514 A1 | 3/2006 |
| WO | WO-2006/047742 A2 | 5/2006 |
| WO | WO-2006/081375 A2 | 8/2006 |

* cited by examiner

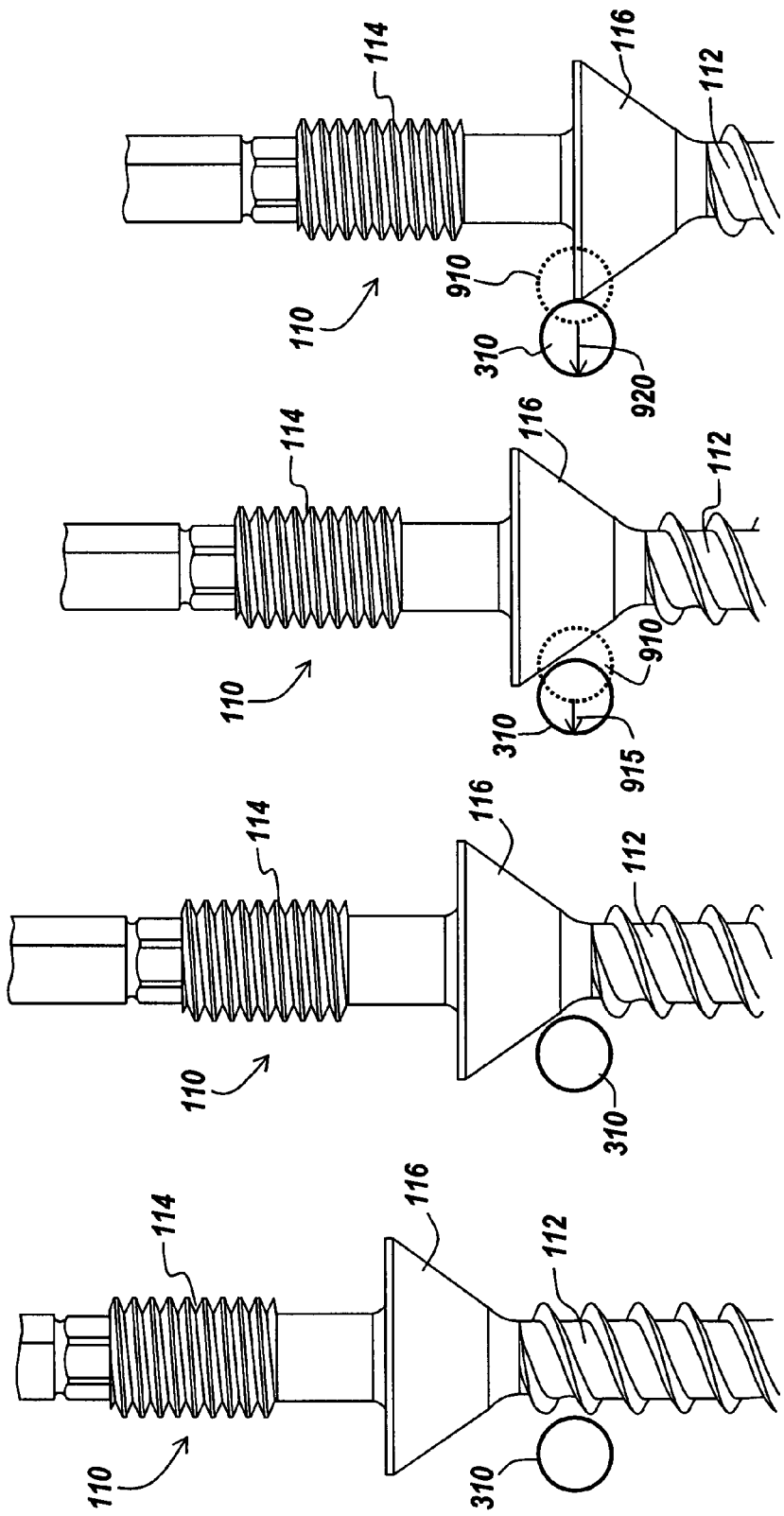

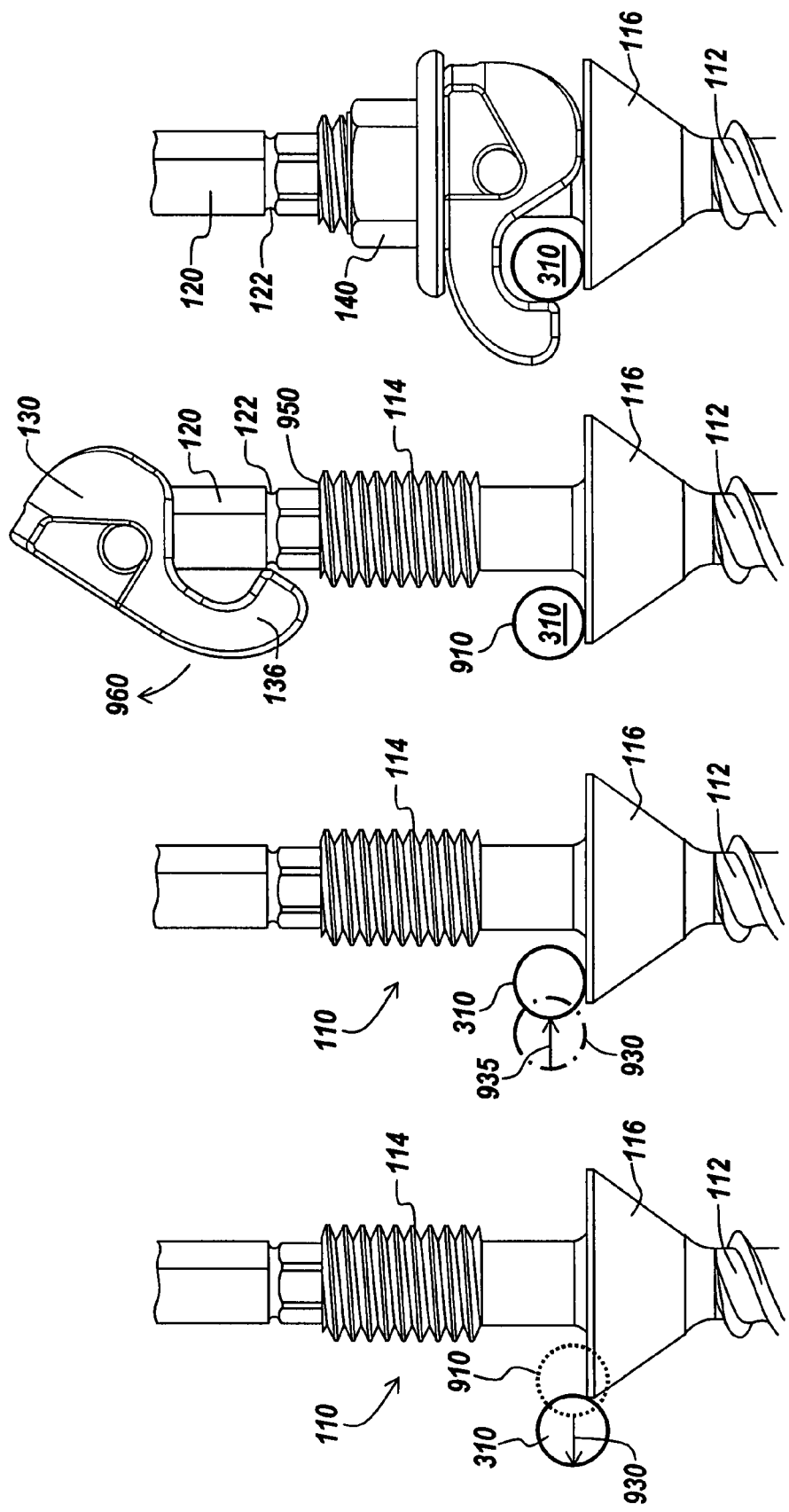

ND SYSTEM FOR SECURING A
METHOD AND SYSTEM FOR SECURING A ROD TO A BONE ANCHOR WITH A CONNECTOR

FIELD OF THE INVENTION

The present invention relates to a spinal connection device and method for use during orthopedic surgery. More particularly, the present invention relates to connector that couples a rod to a bone anchor.

BACKGROUND OF THE INVENTION

Spinal fixation systems may be used in surgery to align, adjust and/or fix portions of a spinal column, i.e., vertebrae, in a desired spatial relationship relative to each other. Many spinal fixation systems employ a spinal rod for supporting the spine and for properly positioning components of the spine for various treatment purposes. Vertebral bone anchors, comprising pins, bolts, screws, and hooks, engage the vertebrae and connect the supporting spinal rod to different vertebrae. Spinal rods can be anchored to specific portions of the vertebra. Since each vertebra varies in shape and size, a variety of anchoring devices have been developed to facilitate engagement of a particular portion of the bone.

Pedicle screw assemblies, for example, have a shape and size that is configured to engage pedicle bone. Such screws typically include a threaded shank that is adapted to be threaded into a vertebra, and a head portion having a spinal fixation element-receiving portion, which, in spinal rod applications, is usually in the form of a U-shaped slot formed in the head portion for receiving the rod. A set-screw, plug, cap or similar type of closure mechanism is used to lock the rod into the rod-receiving portion of the pedicle screw.

In conventional spinal surgery, first, anchoring devices are attached to vertebra, then a spinal rod is aligned with the anchoring devices and secured. For example, for conventional pedicle screw assemblies, first the engagement portion of each pedicle screw is threaded into a vertebra. Once the pedicle screw assembly is properly positioned, a spinal fixation rod is seated in the rod-receiving portion of each pedicle screw head. The rod is locked into place by tightening a cap or similar type of closure mechanism to securely interconnect each pedicle screw to the fixation rod. This type of conventional spinal surgical technique usually involves making a surgical access opening in the back of the patient that is almost as long as the length of the spinal rod to be implanted. Because exact placement of the screw assemblies depends on a patient's particular bone structure and bone quality, the exact position of all screw assemblies cannot be known until after all the assemblies are positioned. Adjustments, such as bending, are made to the spinal rod to ensure that it aligns with each screw assembly.

Recently, the trend in spinal surgery has been moving toward providing minimally invasive surgical (MIS) devices and methods for implanting spinal fixation devices. An example of a minimally invasive method is a rod-first method that includes inserting a spinal rod through a first incision and positioning the spinal rod along a patient's spinal column adjacent to one or more vertebra. After the spinal rod is inserted, one or more bone anchors are inserted adjacent to the spinal rod, each through a separate incision. After a spinal bone anchor is inserted and anchored in bone it is connected to the spinal rod. The rod-first method is a minimally invasive technique in which the bone anchors are inserted adjacent to the rod, after rod insertion, then connected with the rod, as opposed to a conventional surgical technique in which the anchors are inserted first, then the rod is placed such that it lies over the anchors.

Thus there is a need to be able to insert bone anchors, and more particularly connectors for connecting the bone anchors to the rod using minimally invasive techniques. Accordingly, what is needed is a rod anchoring system that can be delivered percutaneously to an implant site though a small access port such as a cannula.

SUMMARY OF THE INVENTION

Embodiments of the present invention provide a rod anchoring system for securing a rod to one or more vertebra of a patient's spine. The connector of the rod anchoring system is configured to be inserted in one orientation and then transitioned to a second orientation to connect the rod to the anchor. The bone anchor may include a detachable extension shaft that acts as a guide for inserting the connector. In use, once the bone anchor has been implanted at a target site on a vertebra, the connector is placed onto bone anchor or the extension shaft and slid along its length in a first orientation to insert the connector. Once the connector is at the implant site, it is transitioned (e.g. swiveled) from the first orientation to the second orientation to connect the rod to the anchor.

In accordance with one aspect, a rod anchor system is provided for use in minimally invasive rod-first spinal fixation. The rod anchor system includes a bone anchor and a connector for connecting a rod to the bone anchor at an implant site, the connector having a channel allowing the connector to slide over the bone anchor for insertion to the implant site. The connector can transition from a first orientation for insertion to a second orientation at the implant site for connecting a rod to the bone anchor.

In certain embodiments, the bone anchor is an anchor bolt. The anchor bolt has a bone engagement portion; a threaded head portion for receiving a locking member; and a rod seat disposed between the bone engagement portion and the threaded head portion for seating a rod. In certain embodiments the anchor bolt may include a detachable extension shaft that extends from the threaded head portion opposite the bone engagement portion.

In certain embodiments, the system further includes a guide system for inserting the bone anchor and connector. The guide system comprises a guide portion, a rod engaging member, and one or more targeting members. The guide portion is adapted to be positioned outside a patient's body and to extend along a patient's spinal column. The rod-engaging member is mated to the guide portion and adapted to couple to the rod and to maintain the rod in a fixed position within the patient's body extending adjacent to a patient's spinal column. The one or more targeting members are slidably coupled to the guide portion. Each targeting member is adapted to target an implant site on a vertebra in the patient's spinal column.

In accordance with another aspect, a method is provided for coupling a rod positioned to extend along a patient's spinal column to a patient's vertebra. The method comprises providing a rod anchor system as set forth above, implanting the bone anchor at an implant site on one of the patient's vertebra, inserting the connector over the bone anchor in the first orientation to the implant site, transitioning the connector from the first orientation to the second orientation at the implant site to connect the rod to the bone anchor, and securing the connection of the rod to the bone anchor.

BRIEF DESCRIPTION OF THE FIGURES

These and other features and advantages of the mechanisms and methods disclosed herein will be more fully understood by reference to the following detailed description in conjunction with the attached drawings in which like reference numerals refer to like elements through the different views. The drawings illustrate principles of the instruments and methods disclosed herein and, although not to scale, show relative dimensions.

FIGS. 9A-9F illustrate the relative positions of the rod, the bone anchor, and the connector, according to aspects of the present invention;

FIGS. 9G-H illustrates the relative positions of the rod, the bone anchor, the connector during the connection of the rod to the bone anchor, according to aspects of the present invention;

DETAILED DESCRIPTION OF THE INVENTION

Certain exemplary embodiments will now be described to provide an overall understanding of the principles of the structure, function, manufacture, and use of the adaptable clamping mechanisms and methods disclosed herein. Examples of these embodiments are illustrated in the accompanying drawings. Those of ordinary skill in the art will understand that the adaptable clamping mechanisms and methods of use specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

System

Figure 1:
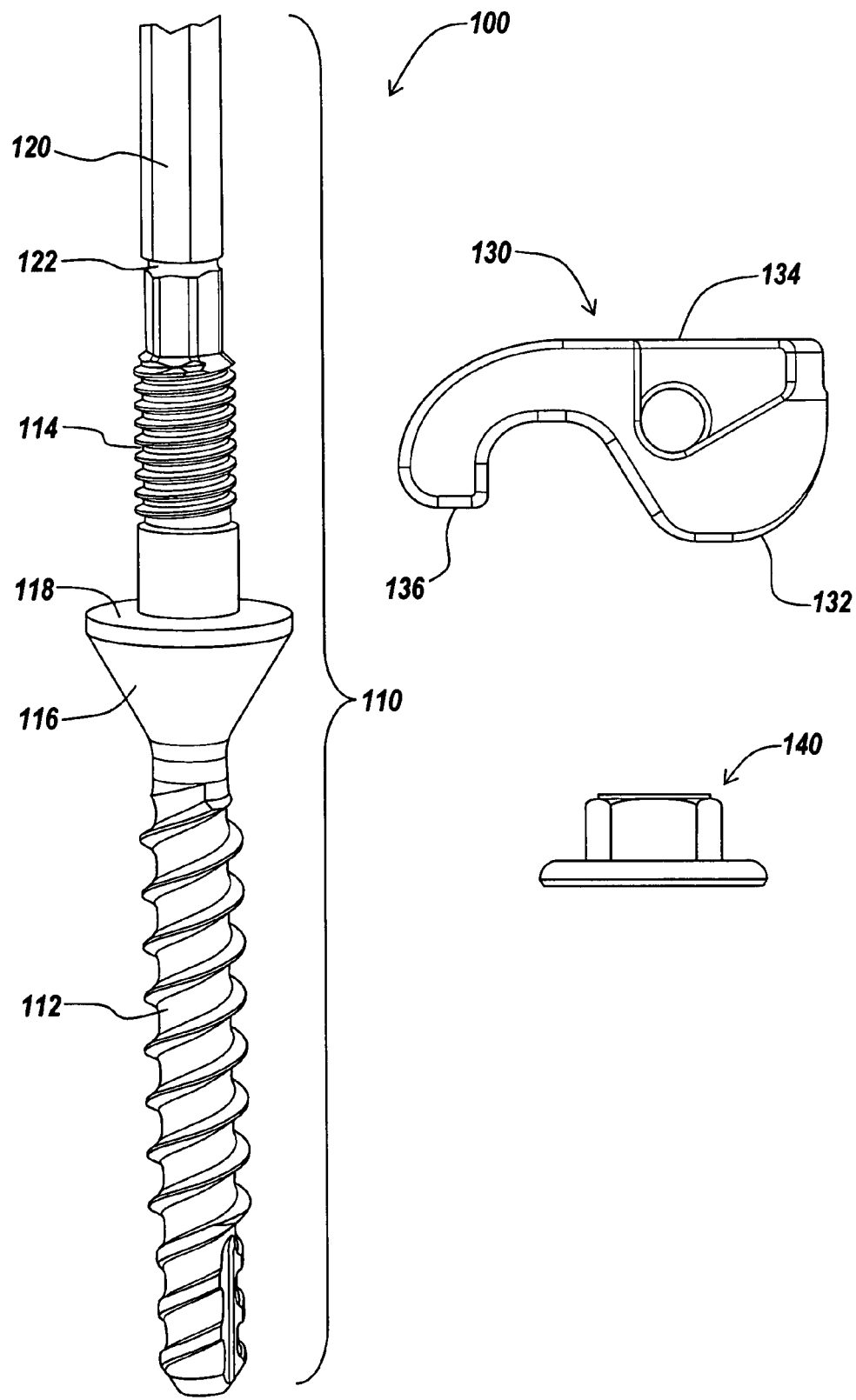
FIG. 1 illustrates components of a rod anchor system in accordance aspects of the present invention.

FIG. 1 depicts one exemplary embodiment of a rod anchor system 100 for use in minimally invasive rod first spinal fixation. The rod anchor system 100 includes a bone anchor 110 and a connector 130 configured to connect a spinal rod (not shown) to the bone anchor 110. In certain embodiments, the system 100 may further include a locking member 140, such as a nut.

In certain embodiment, such as shown in FIG. 1, the bone anchor 110 may include a detachable extension rod 120 to assist in the insertion of the bone anchor 110 and connector 130. The extension rod 120 is configured to extend outside of a patient when the bone anchor 110 is implanted in the patient. As such, the extension rod 120 provides a guide for the insertion of connector 130 and a locking member 140 to the implant site. In certain embodiments, the detachable extension rod 120 has a break-away feature 122 allowing the extension rod 120 to be detached and removed after the connector 130 and locking member 140 have been inserted. Alternatively, the detachable extension shaft 120 can be detached by cutting the shaft away from the anchor bolt 110. Other possible configurations and techniques will be apparent to one skilled in the art given the benefit of this disclosure.

Any number of bone anchors may be used for anchoring a spinal rod. Bone anchor with and without extensions shafts may be used. Preferably, the bone anchor is sized and dimensioned for use in minimally invasive surgical techniques. Furthermore, rod-first techniques make the use of side loading bone anchors for laterally engaging a rod more preferable. In the illustrative embodiments discussed herein, the bone anchor 110 comprises an anchor bolt.

The anchor bolt 110 has a bone engagement portion 112, a threaded head portion 114 for receiving a locking member 140, and a rod seat 116 disposed between the bone engagement portion 112 and the threaded head portion 114 for seating a rod (not shown). In embodiment with detachable extensions, the detachable extension shaft 120 may extend from the threaded head portion 114 opposite the bone engagement portion 112.

In the embodiment of FIG. 1, the rod seat 116 is configured to provide feedback regarding the position of the rod relative to the position of the rod seat 116. In this present example, this involves a flared configuration where the rod seat 116 increases in diameter from the diameter of the bone engagement portion 112 to provide a ledge surface 118 for seating a rod. The interaction of the rod seat and a rod will be discussed in more detail below.

The connector 130 is configured for connecting a rod to the bone anchor 110 at an implant site. The connector is further configured to transition from a first orientation for insertion along the bone anchor 110 to a second orientation at the implant site for connecting a rod to the bone anchor 110. In this embodiment, the connector 130 includes a body 132 and a clamp 136 for capturing a rod to connect the rod to the bone anchor 110. The body 132 defines a channel 134 allowing the connector 130 to slide over the threaded bolt head 114 of the bone anchor 110 for insertion of the connecter 130 to the implant site. In embodiments, with an extension shaft 120, the channel allows the connector to slide along the length of the extension shaft to the implant site. The interaction of the connector with the bone anchor 110, extension shaft 120, and rod can be seen in FIGS. 2 and 3.

Figure 2:
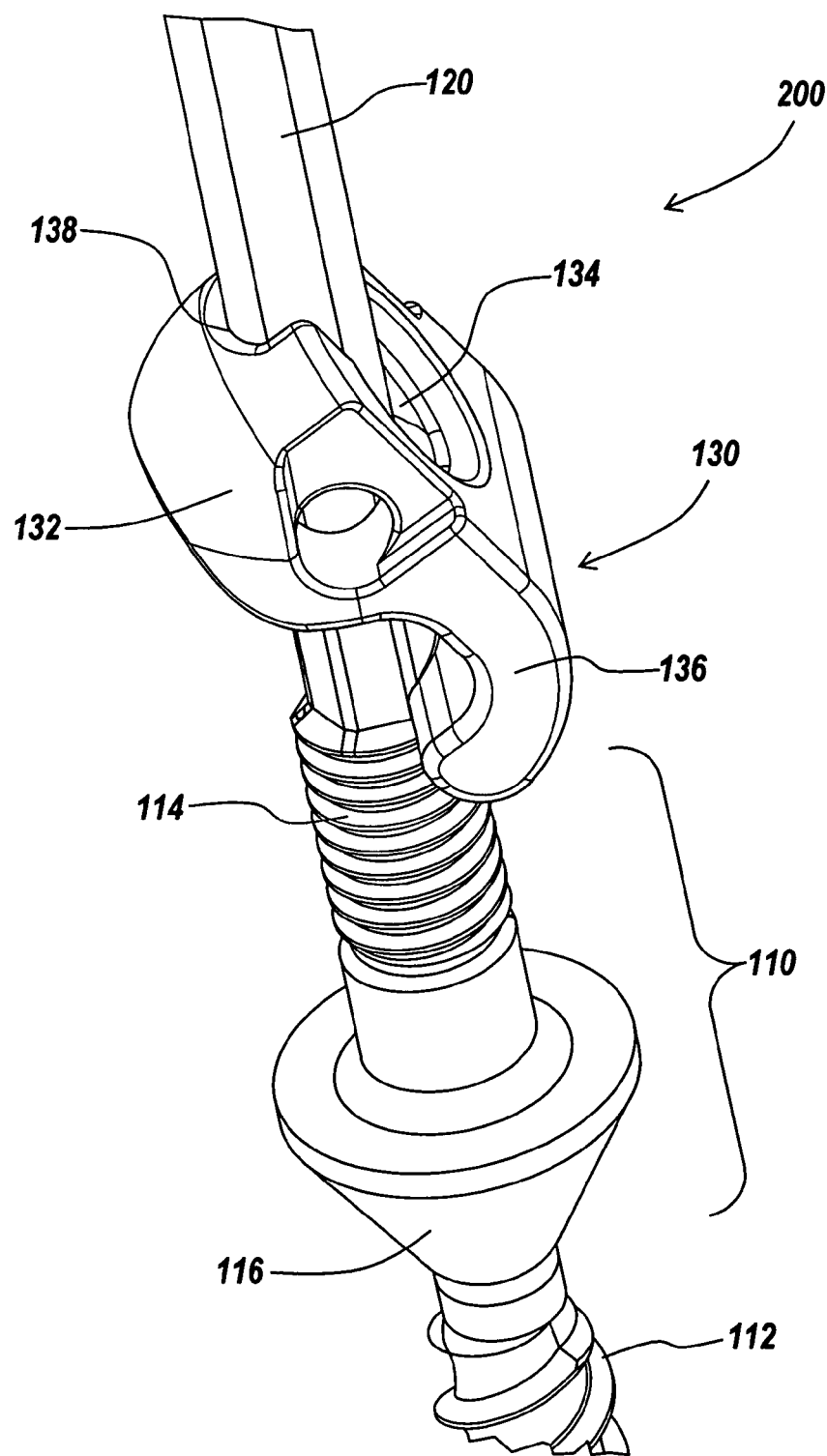
FIG. 2 illustrates an exemplary embodiments of the connector of the rod anchor system in a first orientation for insertion in accordance aspects of the present invention.

FIG. 2 depicts an illustrative embodiment of the rod anchoring system 100 of the present invention wherein the connector is in a first orientation 200 such that the connector 130 is positioned substantially parallel to the extension shaft 120 such that the clamp 136 of the connector 130 is in contact with the extension shaft 120. The first orientation 200 of the connector 130 reduces the profile of the connector 130 so that it may be inserted using minimally invasive surgical techniques. In this example, the channel 134 in the body 132 of the connector 130 is configured to allow the connector 130 to swivel on the extension shaft 120. In this embodiment, the channel 134 provides a cut-away portion 138 that allows the connector 130 to be inserted in a first orientation 200 along the extension shaft 120.

Figure 3:
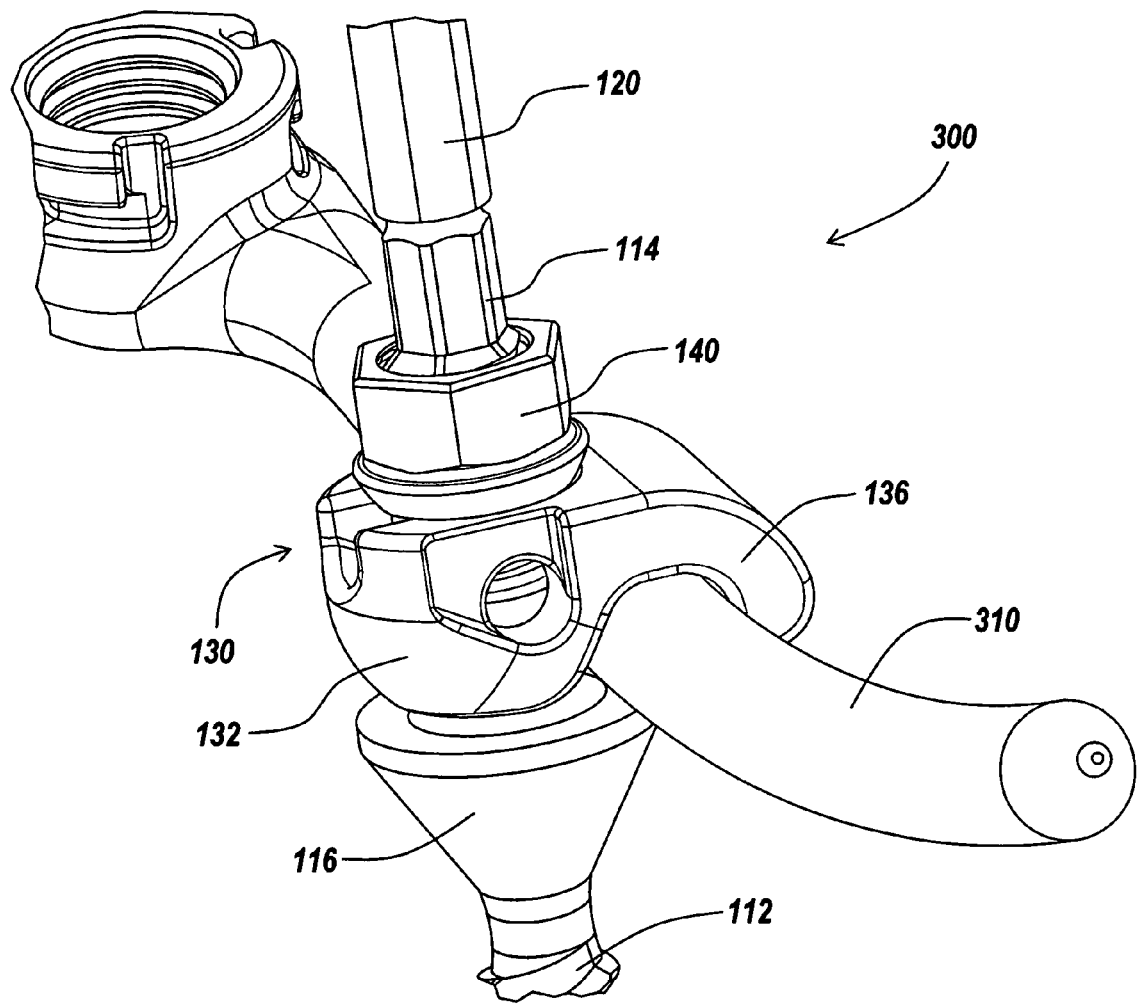
FIG. 3 illustrates an exemplary embodiments of the connector of the rod anchor system in a second orientation connecting a rod to a bone anchor in accordance aspects of the present invention.

FIG. 3 depicts an illustrative embodiment of the rod anchoring system 100 of the present invention wherein the connector has been transitioned to a second orientation 300 to connect a rod 310 to the bone anchor 110. In the second orientation 300, the connector 130 has been swiveled on bone anchor 110 as to be substantially perpendicular to the extension shaft 120 such that the clamp 136 of the connector 130 is able to capture the rod 310 on the rod seat 116 of the bone anchor 110. The connector 130 and rod 310 are secured in position with locking member 140 that engages the threaded bolt head 114 of the bone anchor 110.

As discussed previously, the rod anchor system 100 is preferably configured for use in minimally invasive surgical techniques. As such, the bone anchor 110 and connector 130 are sized and dimension to be inserted to an implant site through an access port such as a cannula. An example of such a cannula 400 can be seen in FIG. 4A-C.

Figure 4A:
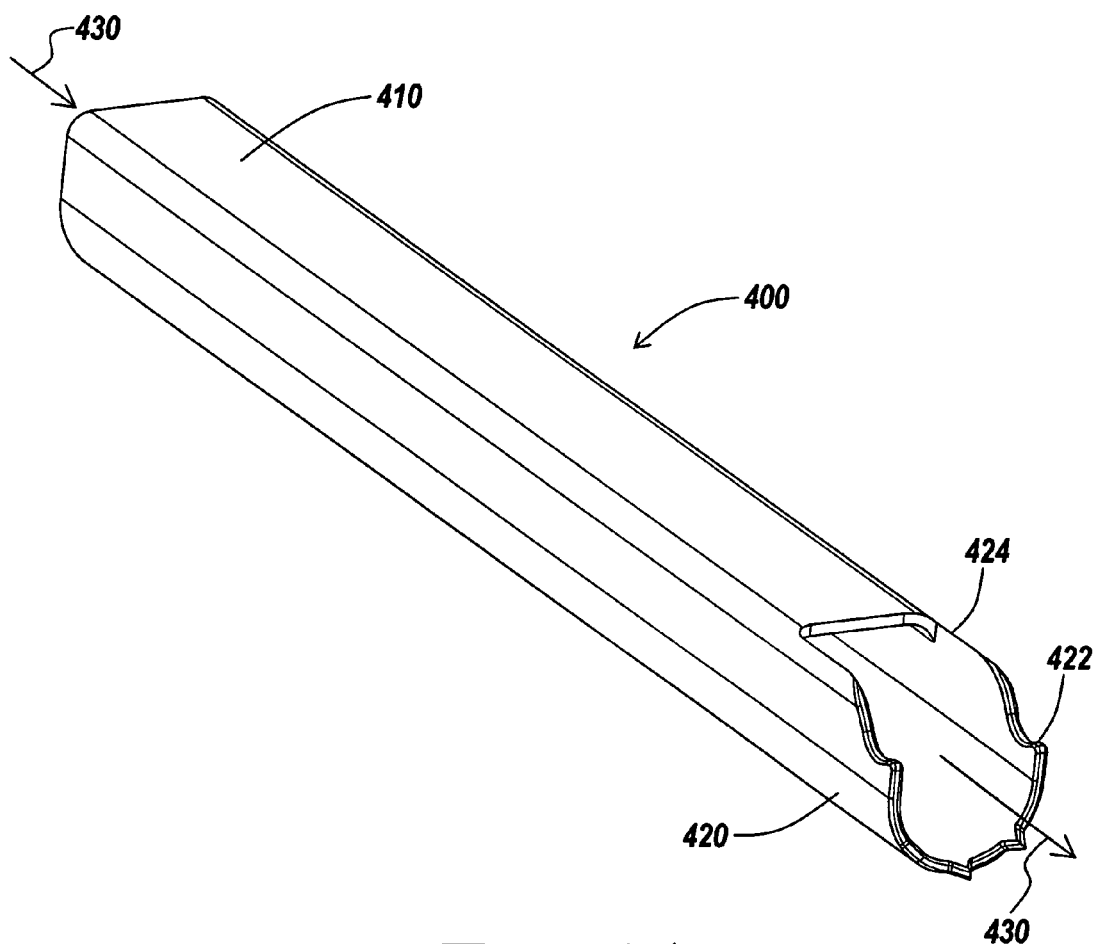
FIG. 4A-C illustrate various views of an exemplary embodiment of a cannula for use with the rod anchor system in accordance aspects of the present invention.

The exemplary embodiment of a cannula illustrated in FIG. 4A has a proximal end 410, a distal end 420, and a central lumen 430 for providing access to an implant site. In use, the distal end 420 is inserted through an incision to an implant site. In certain embodiments, the distal end 420 may have surface configurations 422 for engaging bone on the vertebrae at the implant site. Once inserted, instruments, such as the anchor system 100 of the present invention, may be inserted at the proximal end 410 located outside the patient, and passed along the lumen 430 to the implant site. In some embodiments, the distal end 420 may further include a cut-away or recess 424 allowing a connector 130 to transition from a first orientation to a second orientation at the implant site. Examples of the interaction of the connector 130 with the cannula can be seen in FIGS. 4B and 4C.

Figure 4B:
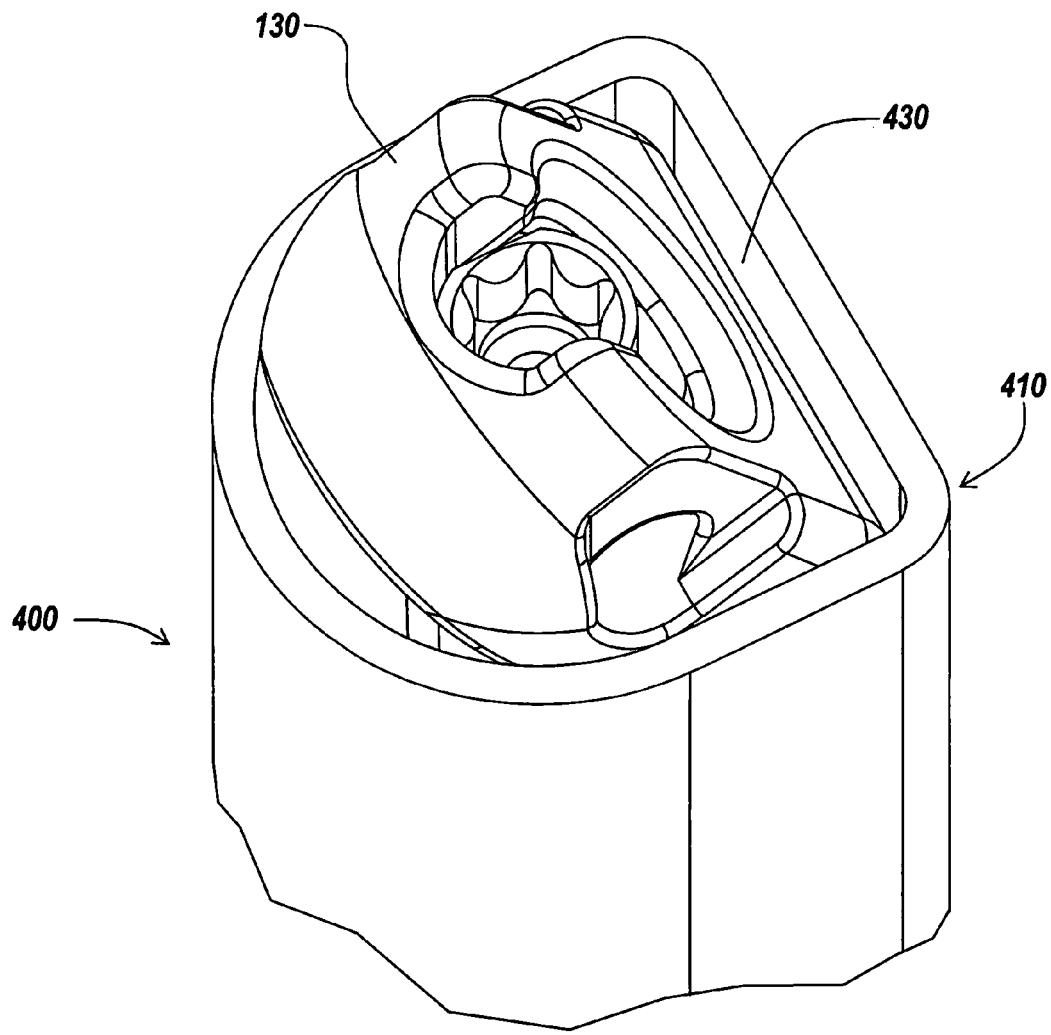

FIG. 4B depicts a magnified view of the proximal end 410 of the cannula 400. Here, a connector 130 is being inserted into the lumen 430 of the cannula 400. In this example, the connector 130 is in first orientation 200 providing the connector 130 with a smaller insertion profile. The cannula 400 is configured to maintain the connector 130 in the first orientation until the connector reaches the implant site.

Figure 4C:
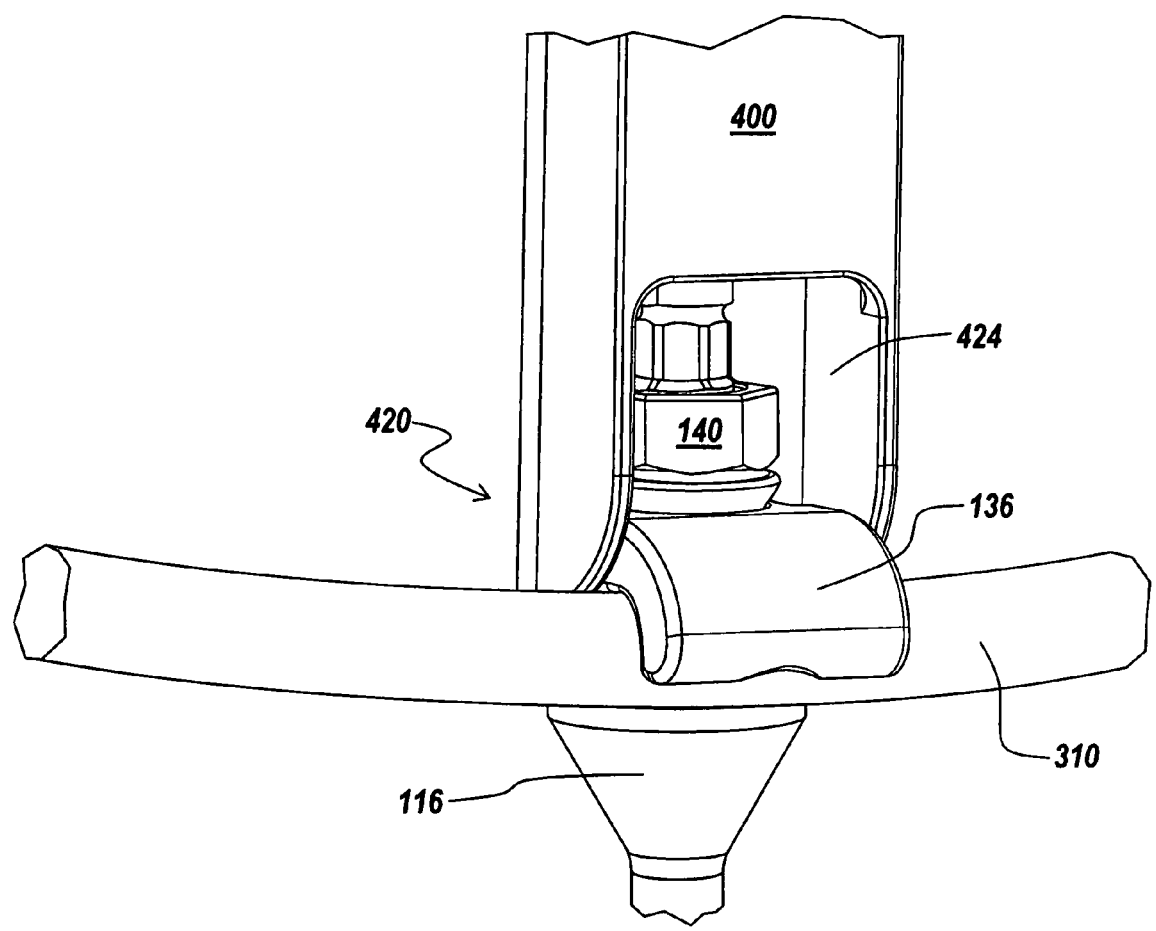

FIG. 4C depicts a magnified view of the distal end 420 of the cannula 400 at an implant site. In this example, a connector 130 that had been inserted in a first orientation at the proximal end 420 of the cannula 400, as shown in FIG. 4B, has been transitioned to a second orientation 300 though recess 424. Once in the second orientation, the clamp 136 of the connector 130 captures the rod 310 on the rod seat 116 of the bone anchor. Locking member 140, also inserted through the cannula 400 secures the swivel connecter 130 and rod 310 to the bone anchor 110

As discussed previously, the rod anchor system 110 of the present invention is designed to be used in minimally invasive rod-first spinal fixation techniques. As such, the rod anchor system 110 may be inserted percutaneously through a separate incision from the incision used to insert the rod. Thus, placement of the rod anchors greatly benefits from the use of a guide system. An example of such a guide system can be seen in FIG. 5.

Figure 5:
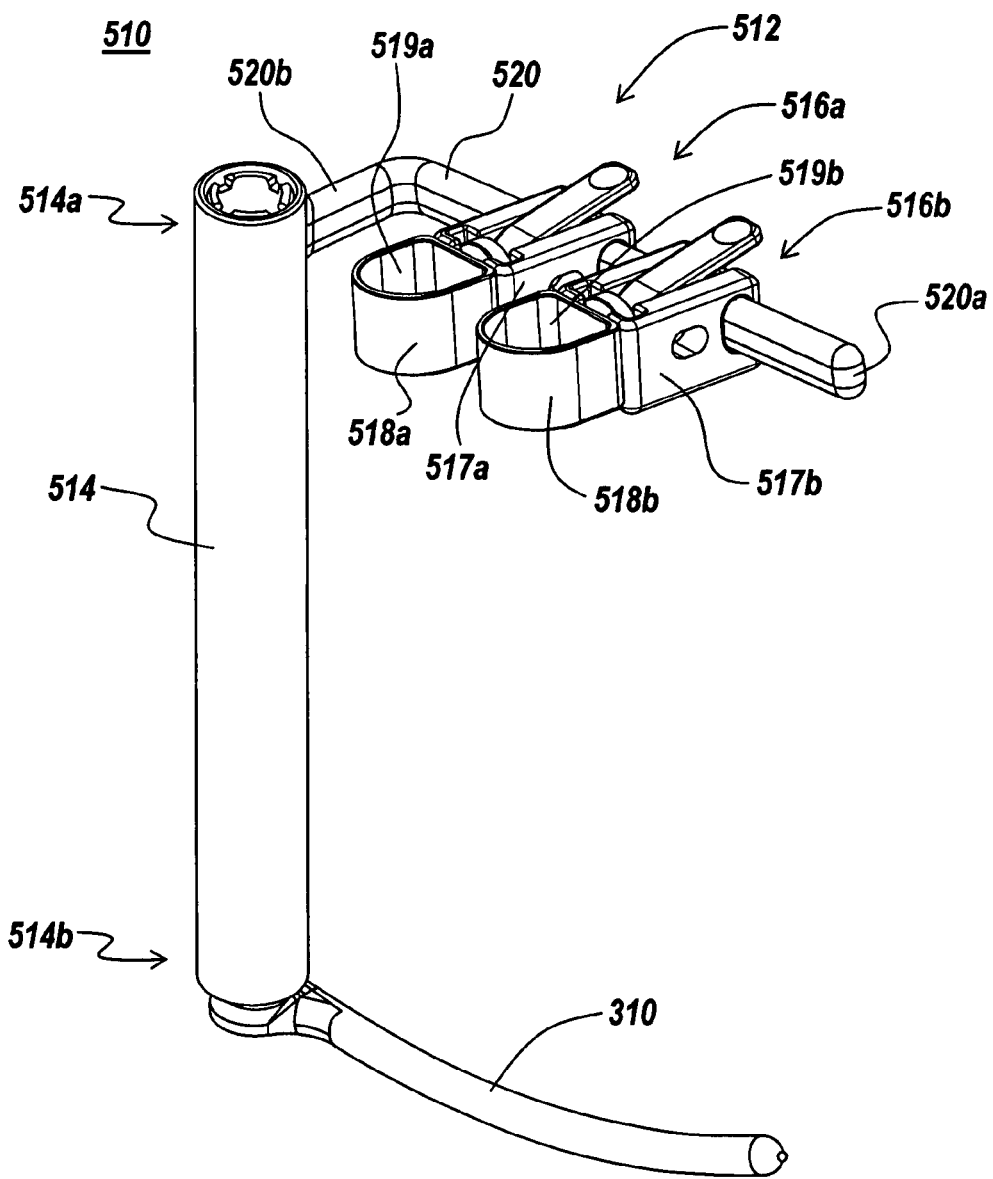
FIG. 5 illustrates an exemplary embodiment of a guide system for use with the rod anchor system in accordance aspects of the present invention.

FIG. 5 illustrates an exemplary embodiment of a guide system 510 (guide system 140 in FIG. 1) that can be used to target implant sites on one or more vertebra and facilitate implanting a rod anchor system. As shown, the guide system 510 generally includes a guide portion 512 that is adapted to be positioned outside a patient's body and a rod-engaging portion 514 that is adapted to couple to a rod 310, to maintain the rod 310 in a fixed position within the patient's body such that the rod 310 extends adjacent to a patient's spinal column. The rod-engaging portion 514 may be effective to maintain the rod 310 in a position that is substantially parallel to, but spaced apart from, the guide portion 512 such that guide portion 512 serves as a guide located outside of the body to indicate the location of the rod 310 disposed inside the patient's body. The guide system 510 can also include one or more targeting instruments 516a, 516b that are movably coupled to the guide portion 512 of the system 510. The targeting instruments 516a, 516b can be adapted to target an implant site on a vertebra in the patient's spinal column.

The guide portion 512 of the guide system 510 can have a variety of configurations. In one embodiment, for example, the guide system 510 is effective to indicate the position of a rod 310 disposed within and extending along a patient's spinal column. As shown in FIG. 5, the guide portion 512 has a generally elongate support rod 520 with opposed first and second ends 520a, 520b. The second end 520b may be adapted to couple to the rod-engaging portion 514. In the illustrated embodiment, the elongated support rod 520 is offset from the rod engaging portion 514 and rod 310 so that targeting instrument 516a, 516b target an implant site in-line with the rod 310.

The rod-engaging portion 514 can have virtually any shape and size. For example, in the illustrated embodiment, the rod engaging portion 514 extends in a direction that is transverse to the support rod 520 and it is adapted to removably engage the rod 310. The first end 514a of the rod-engaging portion 514 may be mated to the second end 520b of the support rod 520, and the second end 514b of the rod-engaging portion 514 is in engagement with a rod 310.

The guide system 510 can also include one or more targeting instruments coupled thereto. As shown in FIG. 5, two targeting instruments 516a, 516b are slidably disposed on the support rod 520 of the guide portion 512. While a variety of targeting instruments and techniques can be employed, in an exemplary embodiment, as shown, one or more of the targeting instruments 516a, 516b may include a slidable support 517a, 517b and a targeting member 518a, 518b coupled to a terminal end of the support 517a, 517b. In certain exemplary embodiments, the targeting members 518a, 518b may be movably coupled to the supports 517a, 517b such that the targeting members 518a, 518b can be moved toward and away from the supports 517a, 517b, as well as angularly adjusted relative to the supports 517a, 517b. Such a configuration allows the targeting instrument 518a, 518b to be properly aligned with a target implant site on a vertebra. While one embodiment for targeting members 518a, 518b can be angularly adjustable, one skilled in the art will appreciate that the members can also be mounted at a fixed angle.

The targeting instruments 516a, 516b, can also be configured to facilitate use of the guide system 510, with other spinal tools and devices. For example, the targeting members 518a, 518b, can include an inner lumen 519a, 519b extending therethrough for receiving spinal tools and devices, such as cannula 400 of FIG. 4. Alternatively, or in addition, the targeting members 518a, 518b, can be removably mated to the slidable support 517a, 517b, to allow each support member 517a, 517b, to mate to a cannula 400 after the targeting members 518a, 518b, are removed. Each support 517a, 517b, can thus be used to maintain a cannula 400 in a fixed positioned relative to a target implant site, thereby providing a guided pathway to a target implant site on a vertebra, as will be discussed in more detail below.

Further discussion of guide systems and their use can be found in DUQ-034 entitled "MINIMALLY INVASIVE GUIDE SYSTEM" filed on Aug. 31, 2007, the content of which is incorporated herein by reference.

Method of Use

Figure 6:
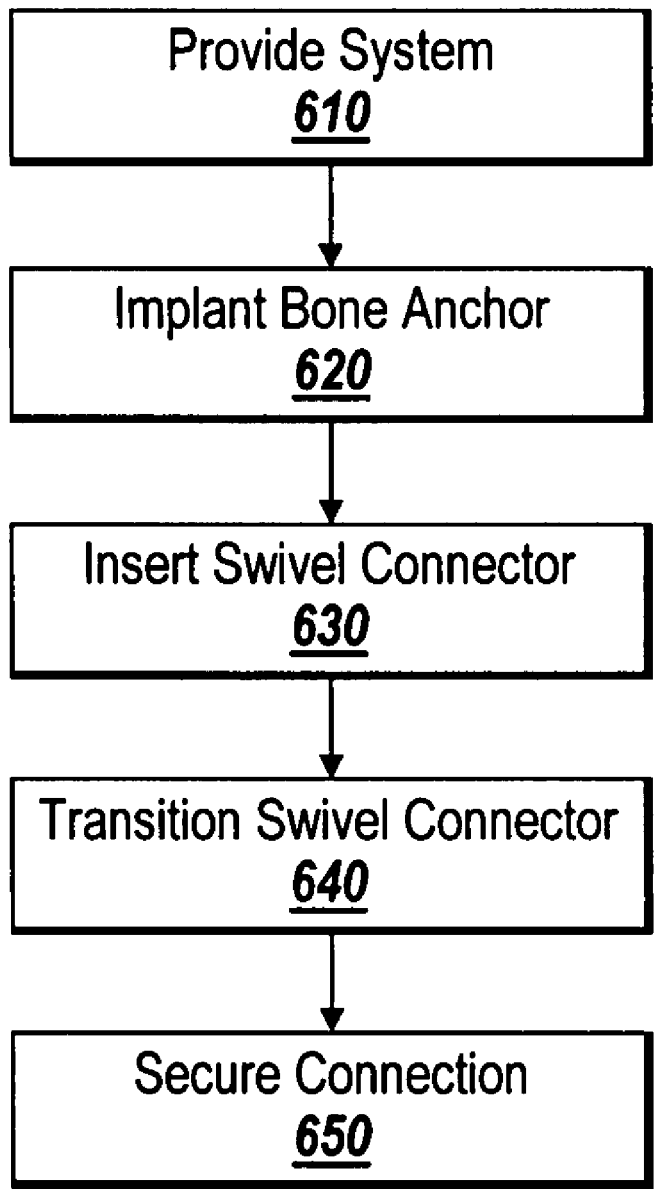
FIG. 6 is a flow chart of one exemplary method in accordance aspects of the present invention.

As previously noted, also disclosed herein are methods for anchoring a rod for spinal fixation. FIG. 6 illustrates a flow chart 600 of an exemplary embodiment of a method. In general, an exemplary method uses the fixation system discussed in FIG. 1 including a bone anchor 110 and connector 130 (step 610). The method further involves implanting the bone anchor 110 at an implant site on one of the patient's vertebra (step 620). Once the bone anchor is implanted, the connector can be inserted along the bone anchor to the implant site in the first orientation (step 630). After the connector has reached the implant site, the connector is transitioned from the first orientation to the second orientation to connect the rod to the bone anchor (step 640). Having connected the rod to the anchor, the connection may then be secured (step 650).

As discussed above, the placement of anchoring systems in minimally invasive rod-first techniques is made significantly easier with the use of a guide system as discussed above in relation to FIG. 5. Therefore in certain embodiments a guide system 510 is attached to the rod 310 to assist in the implantation of the bone anchor 110 and insertion of the connector 130.

Once the rod is attached to the guide system 510 the targeting instruments 516a, 516b can be used to identify a target implant site on one or more vertebrae. In particular, an imaging device can be placed over the targeting members 518a, 518b, to align the targeting members 518a, 518b, with the target implant sites on the underlying vertebra. Once aligned, the targeting members 518a, 518b may be locked in place relative to the support 520 on the guide system 510. The surgeon can then mark the incision location on the skin below the targeting members 518a, 518b.

Once the implant sites on the vertebrae are targeted, the targeting members 518a, 518b, can remain attached to the guide system 510, to allow tools and devices, such as cannulae 400, to be inserted or attached. An example of this can be seen in FIG. 7.

Figure 7:
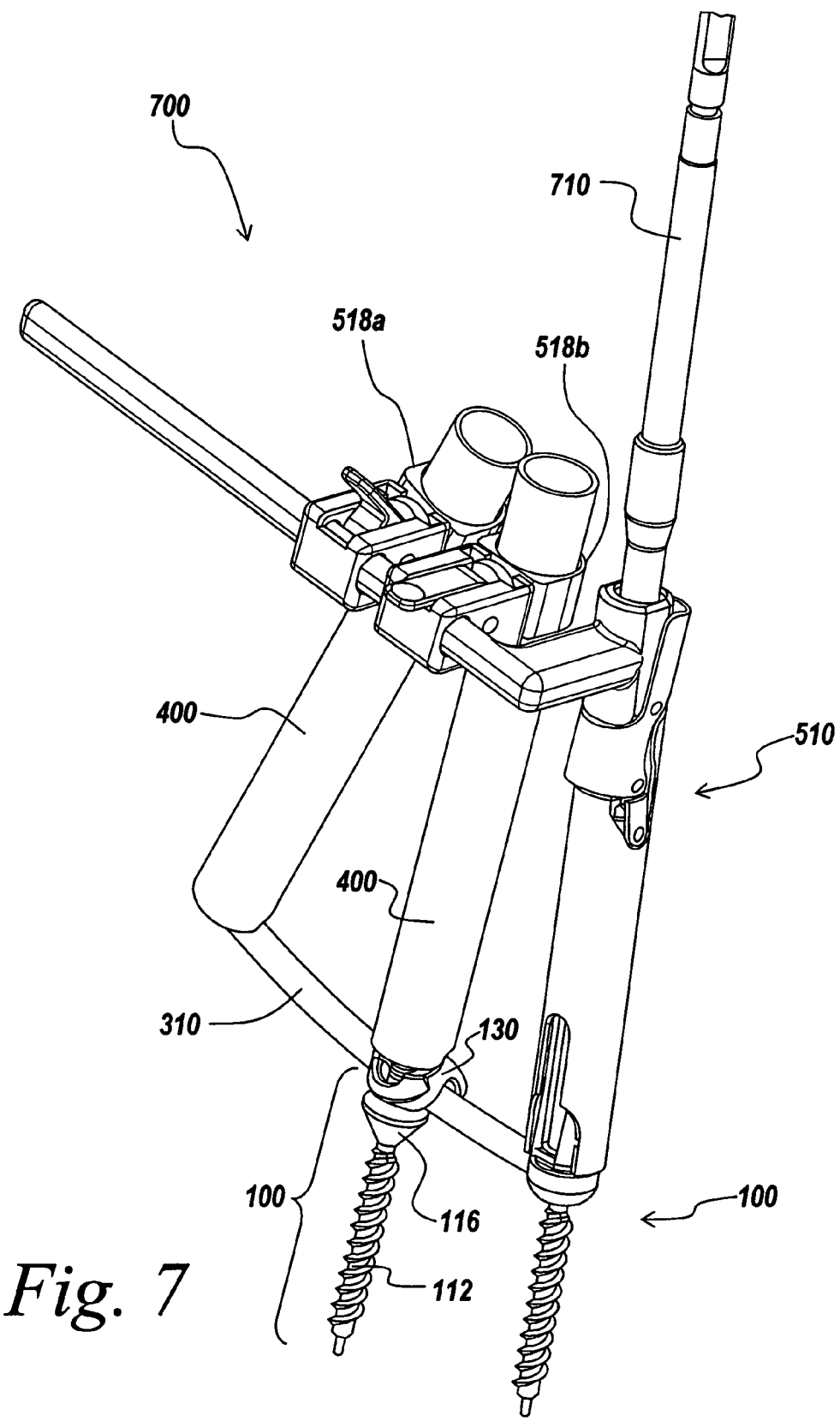
FIG. 7 illustrates an example of a guide system being used to insert rod anchor systems in accordance aspects of the present invention.

FIG. 7 illustrates an exemplary embodiment 700 wherein the guide system 510 of FIG. 5 has been attached to the rod 310 and used to implant the rod anchor system 100 of the present invention through cannula 400 attached to targeting members 518a, 518b of the guide system 510. In this example, installation of the rod anchor system 100 is performed using an installation tool 710.

Figure 8A:
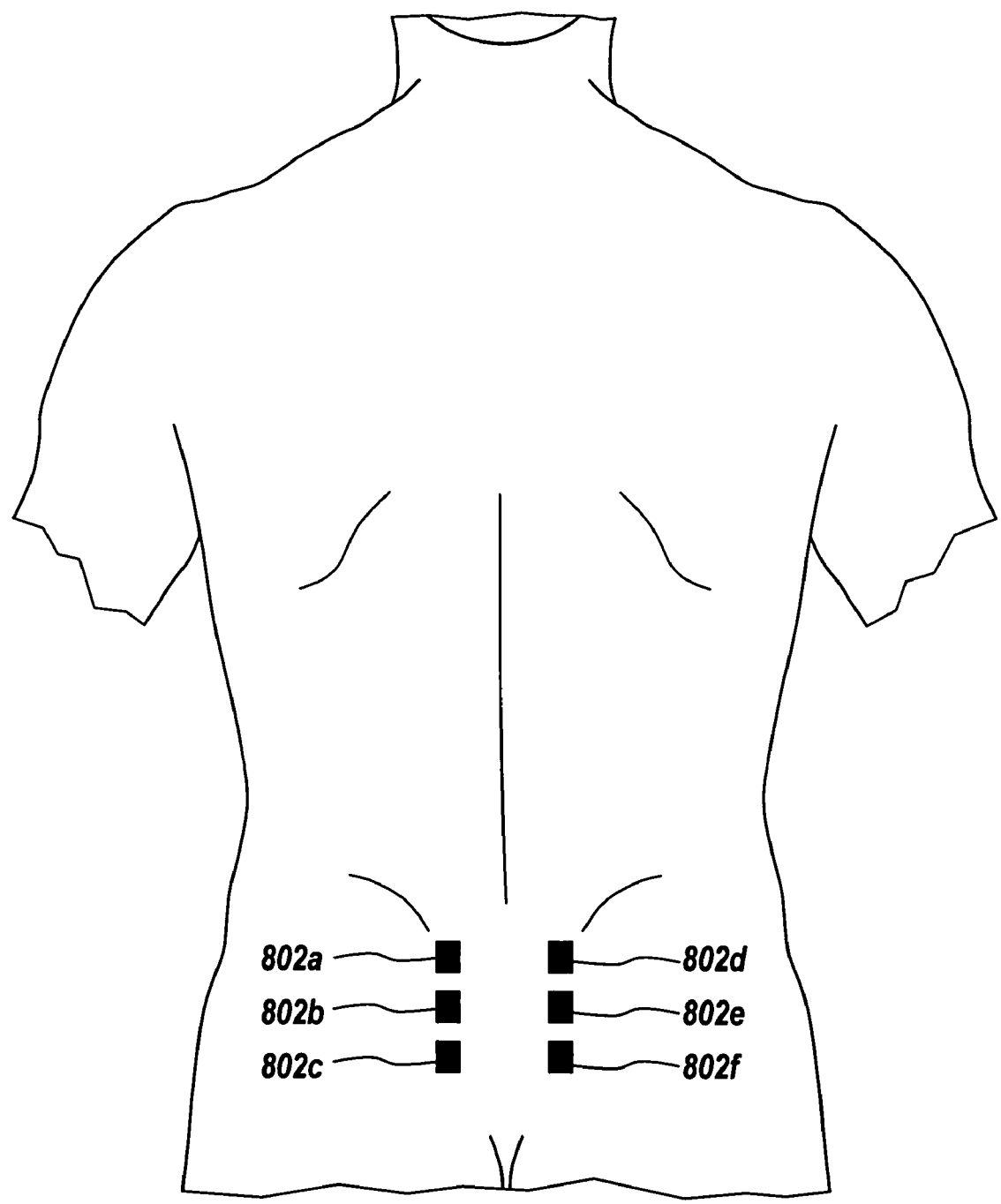
FIG. 8A is a posterior view of six percutaneous incisions formed in the thoracolumbar fascia of a patient's back.

Various techniques can be used to implant the anchors systems; for example a minimally invasive percutaneous incision 802 may be made through the tissue at one or more of the sites. The location, shape, and size of the incision 802 will depend on the type and quantity of rod anchor systems being implanted, as well as the technique being employed to implant the rod anchor systems. By way of non-limiting example, FIG. 8A illustrates three midline minimally invasive percutaneous incisions 802a-c formed on one side of three adjacent vertebra in the thoracolumbar fascia in the patient's back, and three additional minimally invasive percutaneous incisions 802d-f formed on the opposite side of the three adjacent vertebra in the thoracolumbar fascia in the patient's back. While not shown, a guide system 510, can be positioned adjacent to each set of incisions 802a-c, 802d-f with a targeting member in alignment with each incision.

Figure 8B:
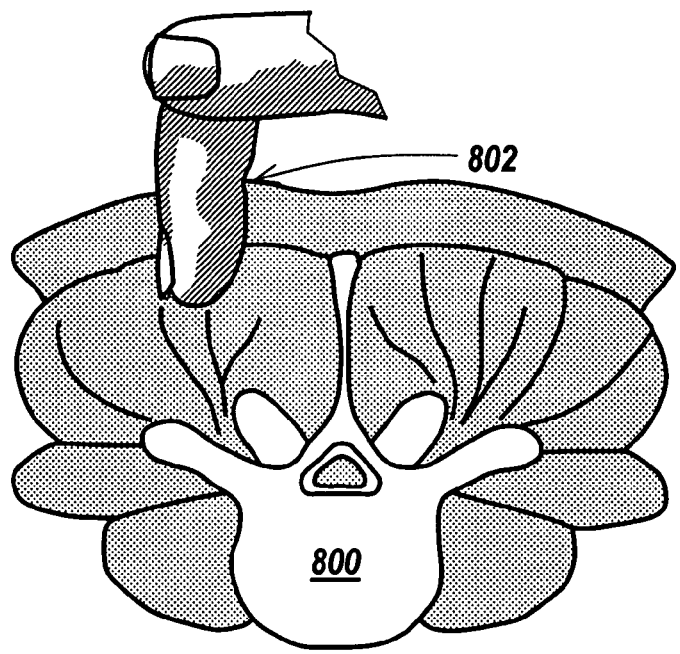
FIG. 8B is an end view showing a blunt dissection of the muscles surrounding a patient's vertebra.

In certain exemplary embodiments, one or more of the incisions may be expanded to create a pathway from the incision 802 to proximate a vertebra 800. For example, the incision 802 may be expanded by serial dilation, with a retractor such as an expandable retractor, or by any other conventional techniques. In one exemplary embodiment, blunt finger dissection can be used, as shown in FIG. 8B, to separate the longissimus thoracis and multifidus muscles, thereby exposing the facet and the junction of the transverse process and superior articular process.

Figure 8C:
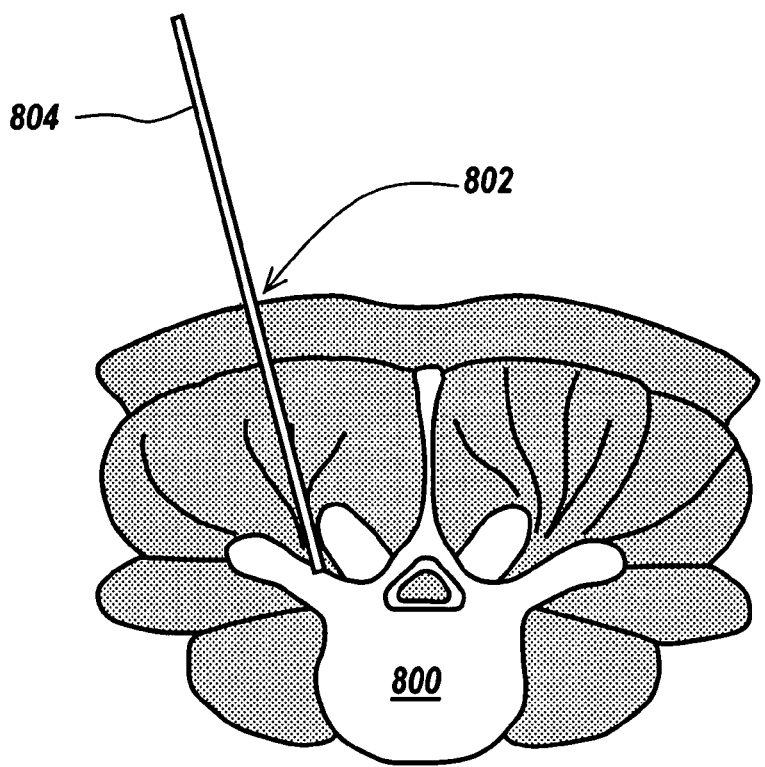
FIG. 8C is an end view of the vertebra in FIG. 8B with a k-wire placed through the incision and into the patient's vertebra.
Figure 8D:
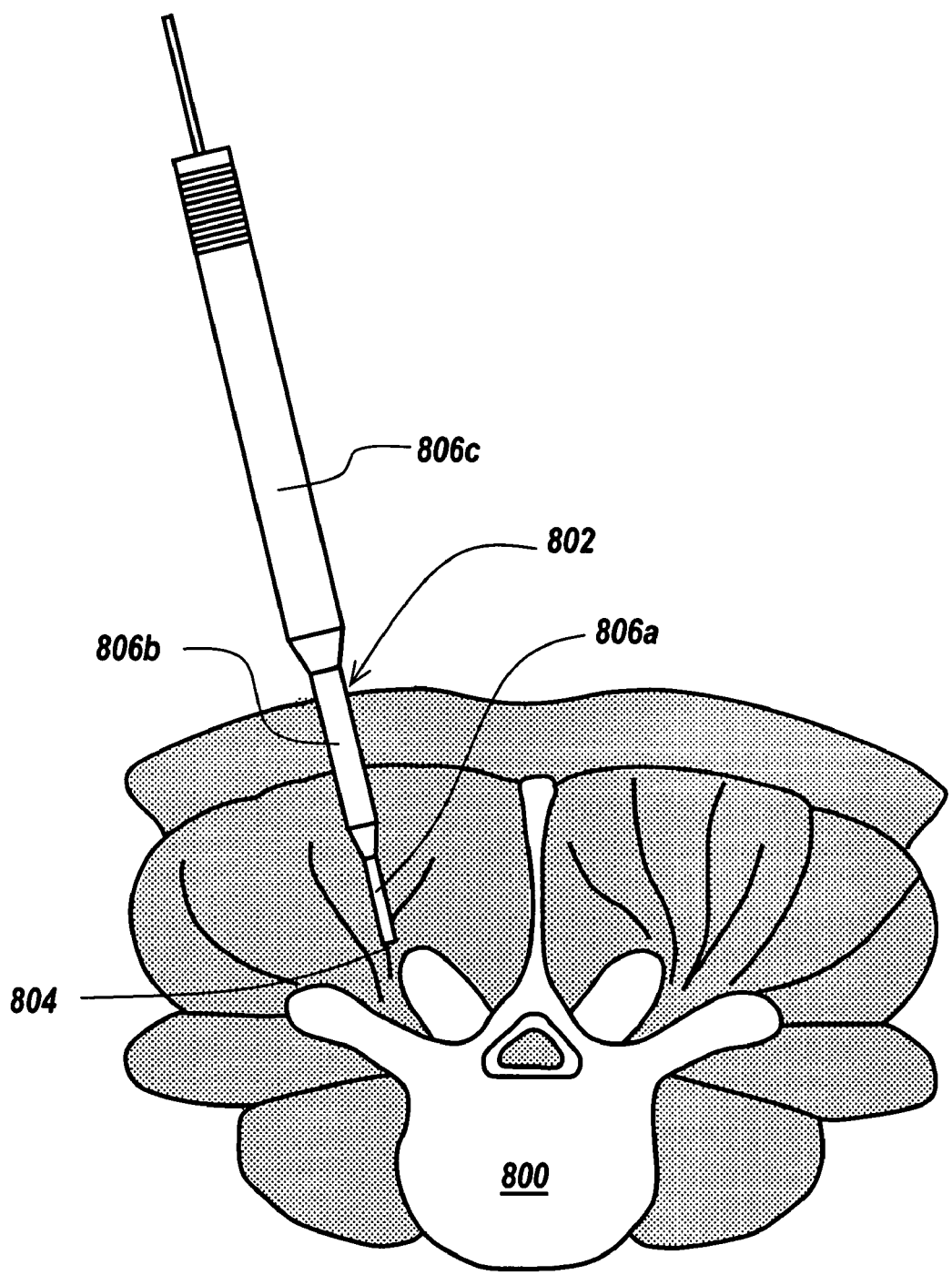
FIG. 8D is an end view of the vertebra in FIG. 8C showing an obturator and several dilators disposed over the k-wire to dilate the tissue and muscles.

A rod anchor system may be inserted through one or more of the incisions and the pathways to proximate the vertebra 800. Any technique for implanting a rod anchor system can be used. In one embodiment, for example, a rod anchor system can be implanted over a guidewire, such as a k-wire. As shown in FIG. 8C, a guide wire, e.g., a k-wire 804, can be implanted, either prior to or after formation of the incision 802, at each rod anchor implant site. The k-wire 804 may extend into the vertebra 800 at the desired entry point of the rod anchor system. In certain exemplary embodiments, the k-wire may be advanced into the vertebra 800. In other exemplary embodiments, the k-wire may be positioned proximate to or against the vertebra 800. Fluoroscopy or other imaging may be used to facilitate proper placement of the k-wire 804. The incision 802 may be dilated to provide a pathway for delivery of a rod anchor system to each implant site, in the manner discussed above, before or after placement of the guidewire. For example, FIG. 8D illustrates serial dilation at one end of the incision 802 using an obturator 806a having several dilators 806b, 806c of increasing size placed there over. The dilators 806b, 806c are delivered over the obturator 806a and k-wire 804 to essentially stretch the skin around the incision 802 and to expand the pathway to the anchor site. While not shown, the obturator 806a and the dilators 806b, 806c can extend through the targeting members 518a, 518b on the guide system 510 or alternatively the targeting members 518a, 518b can be removed from the guide system 510, and the obturator 806a and dilators 806b, 806c can merely be guided along the k-wire.

One skilled in the art will appreciate that a rod anchor system may be advanced to a vertebra through the incision without the need for a guidewire.

Once the incision 802 is dilated to the proper size, if necessary, the vertebra 800 may be prepared using one or more bone preparation instruments, such as drills, taps, awls, burrs, probes, etc. In certain exemplary embodiments, one or more cannulae can be used to provide a pathway from the incision 802 to the anchor site for insertion of the bone preparation instruments and/or the anchor. In an exemplary embodiment, a relatively small cannula 400 (not shown) may be used to introduce bone preparation instruments into the surgical site. The cannula 400 may be placed through a targeting member 518a, 518b on the guide system 510, such that the cannula 400 is in alignment with the target implant site. Once the vertebra 800 is prepared, a rod anchor system can be delivered along the k-wire, either through the cannula 400, or after the cannula 400 is removed, and implanted in the vertebra 800. Alternatively, in embodiments not employing a guidewire, the rod anchor system may be advanced through the incision, e.g., through a cannula 400, to the vertebra 800. A cannula, retractor, or other instrument may be employed to guide the rod anchor system to the vertebra 800.

Although a number of bone anchors are suitable for use with the present invention, in exemplary embodiments discussed herein, the bone anchor used is an anchor bolt as described in relation to FIGS. 1-3 is used to laterally engage the rod. As discussed above, in certain embodiments the rod seat 116 is configured to provide feedback regarding the position of the rod 310 relative to the position of the rod seat. In this present example, this involves a flared configuration where the rod seat 116 increases in diameter from the diameter of the bone engagement portion 112 to provide a ledge surface 118 for seating a rod.

FIGS. 9A-9H illustrate substantially lateral engagement of the rod 310 with the anchor bolt 110 using the connector 130. As illustrated in FIG. 9A, the rod 310 has been inserted into the patent and positioned, and the anchor bolt 110 is being implanted into the patient's vertebra 800 adjacent to the rod 310. In FIG. 9B the anchor bolt 110 has been inserted deep enough that the rod seat 116 comes into contact with the rod 310. In FIG. 9C the anchor bolt 110 has been inserted further and contact between the rod seat 116 and the rod 310 has displaced the rod 310 laterally from its original position 910 by a distance indicated by arrow 915. In FIG. 9D further insertion causes further lateral displacement 920. In FIG. 9E the anchor bolt 110 has been inserted deeper and the rod 310 is at a point of maximal lateral displacement 930.

A shown in FIG. 9F, further insertion of the anchor bolt 110 causes the rod seat 116 to move past the rod 310 causing the rod 310 to "snap" from the position of maximal lateral displacement 930 to its original position 910, a lateral displacement indicated by arrow 935. The sudden change in the position of the rod 310 and the sudden change in lateral force on the anchor bolt 110 may be felt by a surgeon through instruments connected to the anchor bolt 110 providing feedback to the surgeon regarding the position of the rod 310 relative to the rod seat 116. Additionally, the sudden change in the position of the rod 310 and lateral force on the anchor bolt 110 may produce a sound audible to the surgeon. In this manner the rod seat 116 provides auditory and/or tactile feedback regarding a position of the rod 310 relative to a position of the rod seat 116 during insertion of the anchor bolt 110.

After the rod 310 "snaps" back to its original position 910, the rod 310 is properly seated in the rod seat 116. A connector 130 (FIG. 9G) may then be inserted in a first orientation. When the clamp 136 of the connector 130 reaches the bolt head 114 of the anchor bolt 110, surface configurations 950 or the threads on the bolt head 114 cause the clamp 136 to swivel away from the extension shaft 120 as shown by arrow 960. Thus the connector 130 is transitioned to the second orientation for connecting the rod 310 anchor bolt 110 shown in FIG. 9H.

Once the connector 130 is in the second orientation, the clamp 136 captures the rod 310 holding it on the rod seat 116. After the rod 310 is connected to the anchor bolt 110 by the connector 130, the position of the rod 310 and connector may be secured by the a locking member 140 such as a nut configured to engage the threaded bolt head 114 as seen in FIG. 9H.

As discussed previously, in embodiments with detachable extension shafts, the detachable extension shaft 120 of the anchor bolt 110 may include a breakaway feature 122. After the rod 310 is connected and secured by the connector 130, the detachable extension shaft may 120 be separated from the rest of the anchor bolt 110 and removed from the patient. The breakaway feature 122 of the detachable extension shaft 120 may be configured such that a torque force used to tighten the locking member 140 also causes the detachable shaft 120 to separate from the rest of the anchor bolt 110.

A person having ordinary skill in the art will appreciate that the aforementioned methods and devices for implanting rod anchor systems can be modified depending on the type of anchor being implanted, as well as the specific procedure being employed. Moreover, other methods and devices known in the art can be used in accordance with the present invention.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

While the instruments and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

The invention claimed is:

1. A rod anchor system for use in minimally invasive rod first spinal fixation, the rod anchor system comprising:
    a bone anchor extending along an axis; and
    a connector for connecting a rod to the bone anchor at an implant site, the connector having:
        a clamp capturing the rod to connect the rod to the bone anchor; and
        a body defining a channel allowing the connector to slide over the bone anchor for insertion to the implant site,
    wherein the connector can transition from a first orientation for insertion on the bone anchor to a second orientation at the implant site for connecting the rod to the bone anchor,
    wherein the clamp is in contact with the bone anchor in the first orientation;
    wherein the first orientation of the connector is substantially parallel to the axis of the bone anchor and the second orientation is substantially perpendicular to the axis of the bone anchor.

2. The system of claim 1 further comprising a locking member for securing the connector and rod at the implant site.

3. The system of claim 1, wherein the connector swivels from the first orientation to the second orientation.

4. The system of claim 1, wherein the bone anchor further includes surface configurations for transitioning the connector from the first orientation to the second orientation.

5. The system of claim 1, wherein the bone anchor comprises an anchor bolt, the anchor bolt comprising:
    a bone engagement portion;
    a threaded head portion for receiving a locking member; and
    a rod seat disposed between the bone engagement portion and the threaded head portion for seating a rod.

6. The system of claim 5, wherein the anchor bolt further comprises a detachable extension shaft extending from the threaded head portion opposite the bone engagement portion.

7. The system of claim 5, wherein the rod seat is configured to provide feedback regarding the position of the rod relative to the position of the rod seat.

8. The system of claim 1, further comprising a cannula for inserting the bone anchor and connector to an implant site.

9. The system of claim 8, wherein the cannula is configured to maintain the connector in the first orientation during insertion.

10. The system of claim 9, wherein the cannula is configured to allow the connector to transition from the first orientation to the second orientation at the implant site.

11. A rod anchor system for use in minimally invasive rod first spinal fixation, the rod anchor system comprising:
- a bone anchor;
- a connector for connecting a rod to the bone anchor at an implant site, the connector having a channel allowing the connector to slide over the bone anchor for insertion to the implant site, wherein the connector can transition from a first orientation for insertion on the bone anchor to a second orientation at the implant site for connecting a rod to the bone anchor; and
- a guide system for inserting the bone anchor and connector, the guide comprising:
  - a guide portion adapted to be positioned outside a patient's body and to extend along a patient's spinal column;
  - a rod-engaging member mated to the guide portion and adapted to couple to the rod and to maintain the rod in a fixed position within the patient's body extending adjacent to a patient's spinal column; and
  - a plurality of targeting members slidably coupled to the guide portion, each targeting member being adapted to target an implant site on a vertebra in the patient's spinal column.

12. The system of claim 11, wherein the targeting members are removably coupled to support members slidably disposed on the guide portion.

13. The system of claim 12, wherein each support member is adapted to removably mate to a cannula defining a working channel extending to an implant site on a vertebra.

* * * * *